(12) United States Patent
Maier et al.

(10) Patent No.: US 12,709,227 B2
(45) Date of Patent: Aug. 18, 2026

(54) STORAGE ASSEMBLY FOR A VEHICLE AND VEHICLE

(71) Applicant: Mercedes-Benz Group AG, Stuttgart (DE)

(72) Inventors: Valentin Maier, Ispringen (DE); Andreas Sehmsdorf, Althengstett (DE)

(73) Assignee: Mercedes-Benz Group AG, Stuttgart (DE)

( * ) Notice: Subject to any disclaimer, the term of this patent is extended or adjusted under 35 U.S.C. 154(b) by 409 days.

(21) Appl. No.: 18/262,866

(22) PCT Filed: Nov. 30, 2021

(86) PCT No.: PCT/EP2021/083594
§ 371 (c)(1),
(2) Date: Jul. 25, 2023

(87) PCT Pub. No.: WO2022/167119
PCT Pub. Date: Aug. 11, 2022

(65) Prior Publication Data

US 2024/0083363 A1 Mar. 14, 2024

(30) Foreign Application Priority Data

Feb. 2, 2021 (DE) ..................... 10 2021 000 524.4

(51) Int. Cl.
*B60R 7/04* (2006.01)
*A61L 2/10* (2026.01)
*A61L 2/26* (2006.01)

(52) U.S. Cl.
CPC .................. *B60R 7/04* (2013.01); *A61L 2/10* (2013.01); *A61L 2/26* (2013.01); *A61L 2202/11* (2013.01)

(58) Field of Classification Search
CPC ..... B60R 7/04; A61L 2/10; A61L 2/26; A61L 2202/11
See application file for complete search history.

(56) References Cited

U.S. PATENT DOCUMENTS

2012/0248806 A1 10/2012 Enoki
2022/0378957 A1* 12/2022 Hanney ..................... B60R 7/04

FOREIGN PATENT DOCUMENTS

DE 87 08 270 U1 9/1987
DE 198 24 130 A1 12/1999
DE 10 2011 119 425 A1 5/2013
KR 10-1517694 B1 5/2015

OTHER PUBLICATIONS

PCT/EP2021/083594, International Search Report dated Mar. 16, 2022 (Two (2) pages).
German-language German Office Action issued in German application No. 10 2021 000 524.4 dated Oct. 4, 2021 (Six (6) pages).

* cited by examiner

*Primary Examiner* — Nicole M Ippolito
(74) *Attorney, Agent, or Firm* — Crowell & Moring LLP

(57) ABSTRACT

A storage assembly for a vehicle includes a storage compartment for storing an object and a wall where the storage compartment is separated by the wall from a space that has a connecting element for electrical connection of a disinfection module with a vehicle wiring set. The wall has, for access to the connecting element. a predetermined breaking point surrounding a wall section for removing the wall section.

9 Claims, 4 Drawing Sheets

STORAGE ASSEMBLY FOR A VEHICLE AND VEHICLE

BACKGROUND AND SUMMARY OF THE INVENTION

The invention relates to a storage assembly for a vehicle having a storage compartment for storing at least one object. Furthermore, the invention relates to a vehicle having such a storage assembly.

A storage compartment for a vehicle is known from KR101517694 B1, wherein the storage compartment has a wireless charging device and LED modules on two sides of the housing. Furthermore, the storage compartment is constructed to be displaceable in the X direction and the LED modules are constructed in such a way that an object stored in the compartment can be disinfected.

The object of the invention is to provide a storage assembly for a vehicle having a storage compartment and a vehicle having such a storage assembly.

A storage assembly for a vehicle comprises a storage compartment for storing at least one object. It is provided according to the invention that the storage compartment is separated, by means of a wall, from a space having a connecting element for the electrical connection of a disinfection module for disinfecting the object stored in the storage compartment with a vehicle wiring set, wherein the wall for access to the connecting element has a predetermined breaking point surrounding a wall section for removing this wall section.

Because the wall section of the wall of the storage compartment is detachable, the disinfection module can be integrated into the storage compartment simply and without great effort, provided that this is desired by a vehicle user of the vehicle as a feature. The storage assembly can therefore be used both in a vehicle without a requested disinfection module and also in a vehicle in which a disinfection module is to be integrated, so that costs arise and integration efforts can be saved.

Such a storage assembly can be adapted in relation to different models or vehicles, wherein infrastructure available in the vehicle is respectively used. The arrangement of the disinfection module therefore does not require any variant creation, so that the storage compartment looks fundamentally the same with and without the disinfection module.

It is additionally possible to integrate the disinfection module into the storage compartment as a retrofit solution if this is requested by a vehicle user.

An interface of a serial bus system exists and can be used inside the storage compartment, even if a disinfection module is integrated into the storage compartment.

An embodiment of the storage assembly provides that at least one through-hole for applying a fastening element is inserted into the wall for fastening the disinfection module to the wall. This at least one through-hole serves for the insertion of a screw, by means of which the disinfection module can be fastened to the wall. The dimensions of the through-hole are chosen here in such a manner that, when such a disinfection module is not assembled, it can be ruled out as far as possible that an object stored in the storage compartment will fall through.

If the arrangement of a disinfection module is not provided, the at least one through-hole can serve for ventilating the storage compartment, wherein, by means of the at least one through-hole, air can circulate.

Alternatively or additionally to the at least one through-hole in the wall, a further embodiment provides that at least one shaped element for the form-fitting fastening of the disinfection module to the wall is formed on the wall. The at least one shaped element can be formed here as a locking tab, which corresponds to a further shaped element which is correspondingly formed on the disinfection module, in order to produce the shaped element between the wall and disinfection module.

In an embodiment of the storage assembly, the wall section is connected with the wall by means of a number of connection points, wherein the connection points are broken to remove the wall section and the connection points therefore form part of the predetermined breaking point surrounding the wall section.

In a further embodiment, the wall section is a rectangular shape, so that the disinfection module partially rests on the wall in order to fasten the disinfection module to the wall and so that heat arising during the operation of the disinfection module can be dissipated from the storage compartment by means of an opening arising by means of the removal of the wall section.

In a further embodiment, the disinfection module has at least one UV-C radiation-emitting light source and a further connecting element corresponding to the connecting element, so that the disinfection module can be supplied with the necessary electrical energy for its operation. If the further connecting element is connected with the connecting element, it is possible, in particular during the operation of the vehicle, to disinfect an object stored in the compartment, for example a key belonging to the vehicle user, by means of the disinfection module.

In a further embodiment of the storage assembly, a housing of the disinfection module has a number of air vents on an underside and/or on a rear side facing the wall, so that the heat arising during the operation of the disinfection module can be efficiently dissipated by means of the ventilation openings and the opening in the wall, so that an overheating of the disinfection module can be counteracted as far as possible.

In a further possible embodiment, a number of centring ribs are additionally formed on a rear side of the housing of the disinfection module, wherein arranging the disinfection module optimally aligned in relation to the opening in the wall is enabled without great effort by means of the centring ribs. Equipping the vehicle with the disinfection module in the storage compartment in a shorter time is thereby possible, since the centring ribs form a mounting aid for arranging the disinfection module on the wall.

Furthermore, the invention relates to a vehicle having a storage assembly, which comprises a storage compartment in which, when a disinfection module is desired, this can be integrated into the storage compartment without great effort, wherein, to this end, the wall section can be removed from the wall. If the disinfection module is integrated into the storage compartment and is supplied with electrical energy, an object stored in the storage compartment can be disinfected, in particular during the driving operation of the vehicle.

Exemplary embodiments of the invention are illustrated in greater detail below by means of drawings.

DETAILED DESCRIPTION OF THE DRAWINGS

Figure 1:
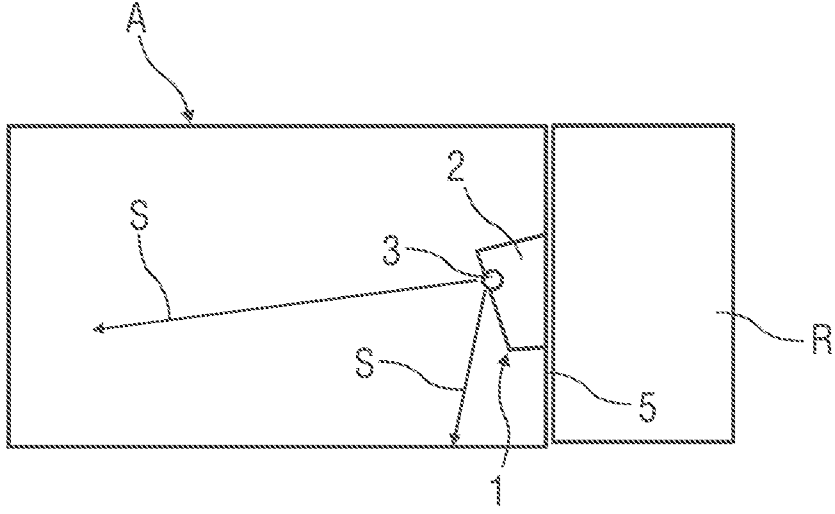
FIG. 1 is a sectional view of a storage compartment having a disinfection module.

Parts that correspond to one another are provided with the same reference numerals in all figures.

FIG. 1 shows a sectional view of a storage compartment A of a storage assembly for a vehicle (not shown in more detail), having a disinfection module 1.

The disinfection module 1 comprises a housing 2 in which a UV-C radiation S-emitting light source 3 and at least one cooling element (not shown in more detail) are arranged, and a further connecting element 4 corresponding to an on-board connecting element on the housing 2. The further connecting element 4 can be connected with the on-board connecting element of a vehicle wiring set, in particular a LIN bus, so that the disinfection module 1 can be supplied with electrical energy for its operation.

The UV-C radiation S-emitting light source 3 is positioned and aligned in such a way that an object stored in the storage compartment A, for example a key or a smartphone of a vehicle user, can be disinfected by means of the UV-C radiation S during the driving operation of the vehicle.

In order to form the storage compartment A without additional variance in such a manner that the disinfection module 1 can be integrated into the storage compartment A as a desired optional extra of the vehicle without great effort, the storage compartment A can, however, also be used for storing an object without the disinfection module 1, the storage compartment A is formed as described in the following.

Figure 4:
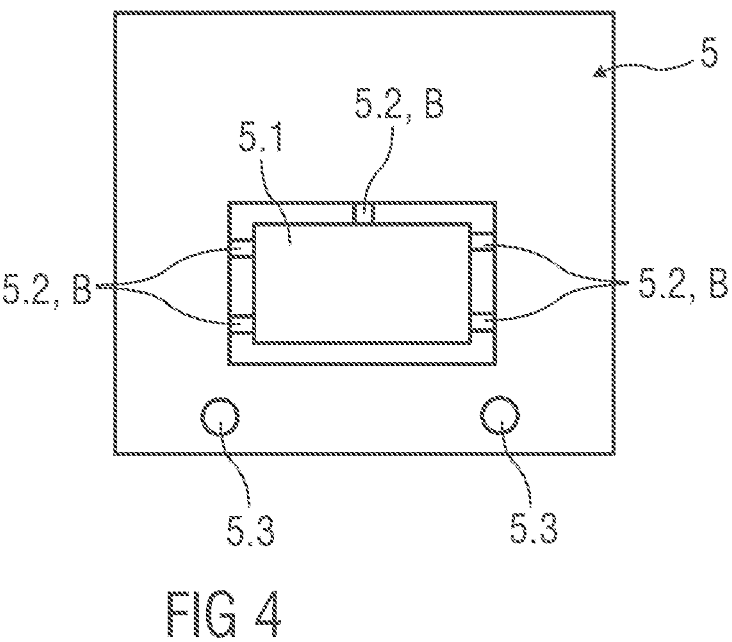
FIG. 4 shows the wall of the storage compartment having a removable wall section.

Since the disinfection module 1 cannot be completely integrated into the storage compartment A due to the available installation space, a wall 5 of the storage compartment A is formed in such a manner that the wall 5 has a removable rectangular wall section 5.1, exemplarily shown in FIG. 4, for access to the on-board connecting element.

Figure 3:
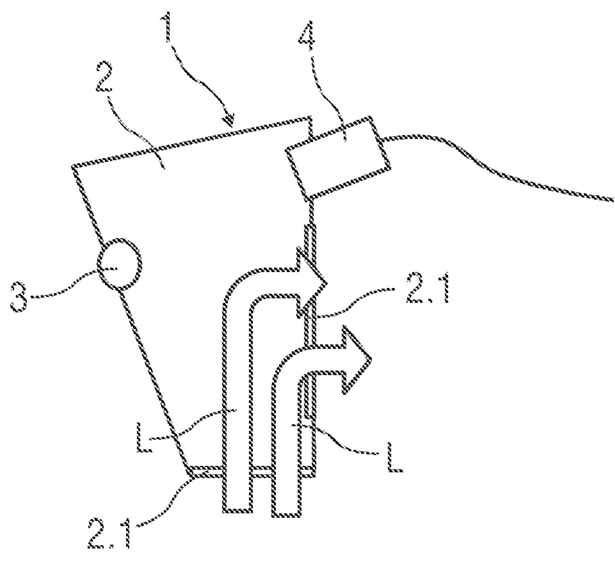
FIG. 3 is a sectional view of the disinfection module in the alternative embodiment.

A predetermined breaking point B surrounds this removable wall section 5.1, which is formed, for example, by means of a number of connection points 5.2 shown in FIG. 3. Alternatively or additionally to the connection points 5.2, the surrounding predetermined breaking point is formed for removing this wall section 5.1 as perforations.

Once again, alternatively or additionally, the wall section 5.1 can itself be formed from a weakened material, wherein in particular a wall thickness of the wall section 5.1 is formed to be thinner than a wall thickness of the wall 5.

Figure 5:
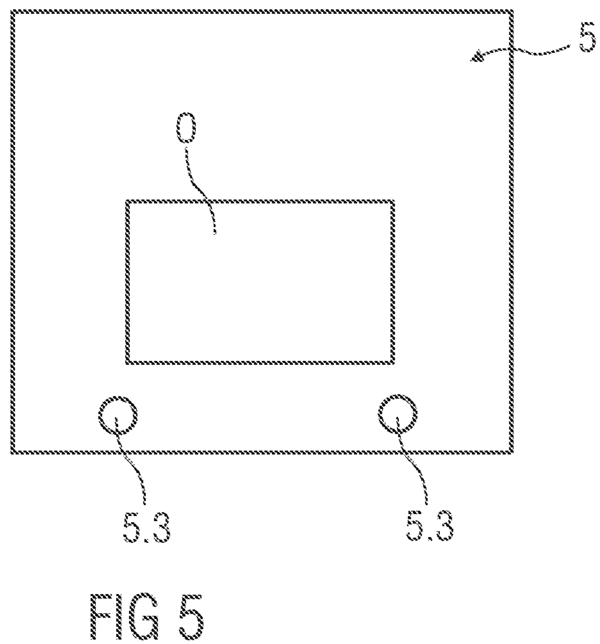
FIG. 5 shows the wall with the removed wall section.

If the integration of such a disinfection module 1 is desired, the wall section 5.1 is broken off the wall 5, for example on the assembly line during the production of the vehicle, in order to create an opening O in the wall 5, in particular shown in FIG. 5.

In a space R separated from the storage compartment A by means of the wall 5, the on-board connecting element is arranged for connection with the further connecting element 4 of the disinfection module 1 and is accessible through the opening O, so that both connecting elements 4 can be connected with each other to install the disinfection module 1. Even when the wall section 5.1 is removed, the on-board connecting element is substantially not visible through the opening, wherein the connecting element is covered by the remaining wall 5.

Figure 2:
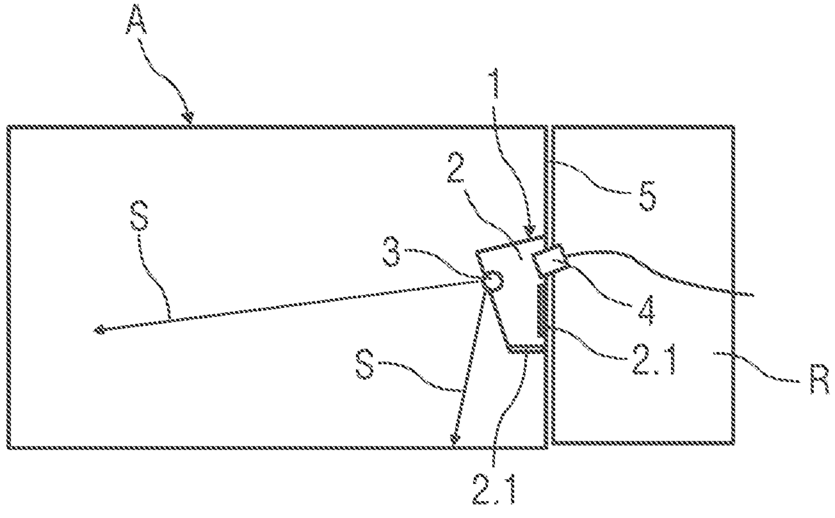
FIG. 2 is a sectional view of the storage compartment having a disinfection module in an alternative embodiment.

FIG. 2 shows a sectional view of the storage compartment A having a disinfection module 1 in an alternative embodiment, wherein an enlarged section of a sectional view of the disinfection module 1 is shown in FIG. 3.

As described above, the disinfection module 1 comprises the housing 2, which has a number of ventilation openings 2.1 for realizing a thermal discharge approach, which are formed on an underside as well as on a rear side of the housing 2. In particular, the air openings 2.1 are formed to be channel-shaped, as is shown in FIG. 3, so that air L can circulate through the disinfection module 1 past the at least one cooling element. It is therefore possible to dissipate heat arising during the operation of the disinfection module 1 from this through the opening O in the wall 5 of the storage compartment A. In particular, the air L is supplied to the space R, in particular the technical space R behind the wall 5, wherein the opening O in the wall 5 is, to this end, correspondingly large, i.e., has corresponding dimensions.

FIGS. 4 and 5 show the wall 5, wherein the wall 5 is shown in FIG. 4 with the removable wall section 5.1 and in FIG. 5 without the wall section 5.1. In particular, the wall 5 is arranged in the storage compartment A without the removed wall section 5.1, i.e., without the opening O, if the arrangement of a disinfection module 1 is not provided.

As is shown in FIG. 4, the wall section 5.1 is connected with the wall 5 by means of the connection points 5.2, wherein the connection points 5.2 can be broken out as predetermined breaking point B to remove the wall section 5.1.

The connection points 5.2 in particular break up when there is pressure exerted on these, wherein, to this end, a screwdriver can, for example, be inserted.

Alternatively or additionally, the wall section 5.1 can have a wall thickness, as described above, so that the wall section 5.1 can be broken off if necessary.

Figure 6:
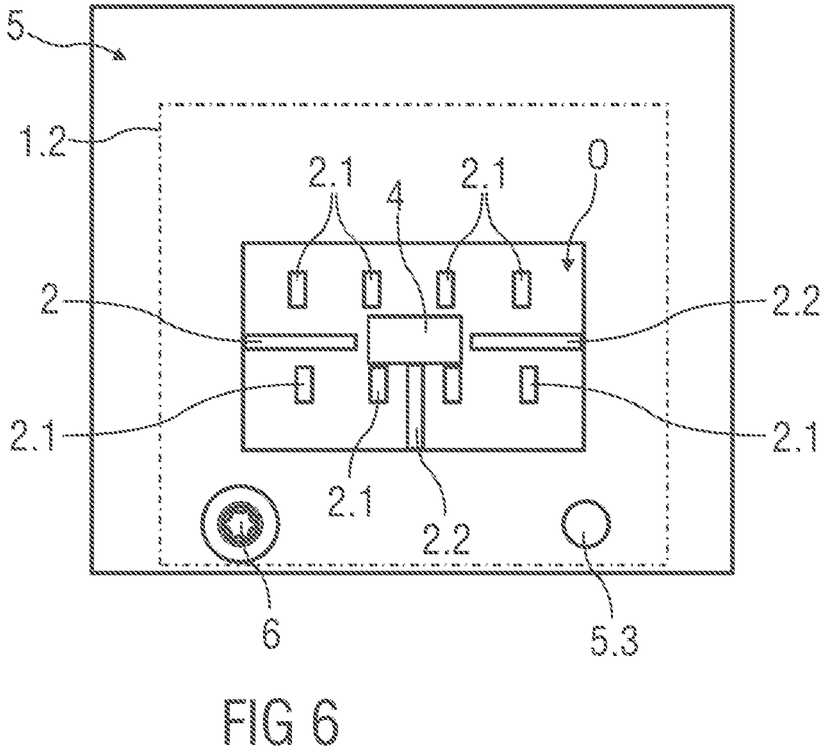
FIG. 6 shows a rear side of the wall with the partially fixed disinfection module.
Figure 7:
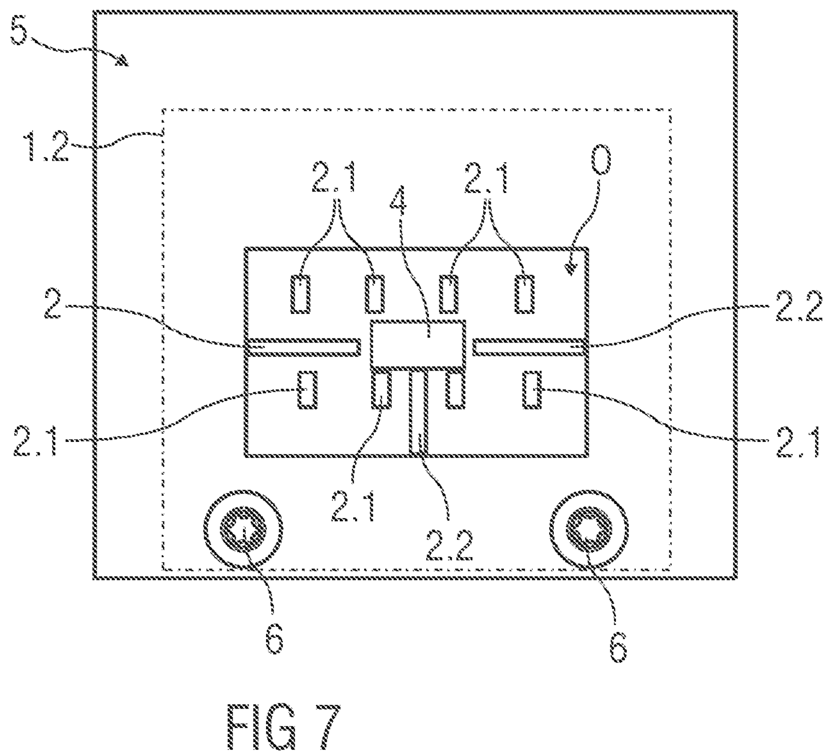
FIG. 7 shows the rear side of the wall with the fully fixed disinfection module.

For fastening the disinfection module 1 to the wall 5, this has two through-holes 5.3 as screw holes according to the present exemplary embodiment in FIGS. 4 to 7, for passing through each of the screws 6 shown in FIGS. 6 and 7.

In an alternative embodiment of the wall 5 not shown in more detail, a number of shaped elements for the form-fitting fastening of the disinfection module 1 to the wall 5 are formed on this alternatively or additionally to the through-holes 5.3. For example, the shaped elements are formed as latching lugs, wherein the disinfection module has shaped elements corresponding to this, in particular on its rear side, so that a latching connection can be produced between the disinfection module 1 and the wall 5, e.g., in the form of a clip.

FIG. 6 shows a rear side of the wall 5 of the storage compartment A having a disinfection module 1 fixed to its front side, wherein its further connecting element 4 and the ventilation openings 2.1 are shown on the rear side of the disinfection module 1. In particular, an outline of the fastened disinfection module 1 is shown by means of a dot-dash line.

Three centring ribs 2.2 are additionally formed on the rear side of the disinfection module 1, in particular of the housing 2, which are provided as mounting aids for aligning the disinfection module 1 in relation to the opening O. Two centring ribs 2.2 are formed horizontally here, and one centring rib 2.2 is formed running vertically on the rear side of the disinfection module 1.

If the disinfection module 1 is positioned aligned on the wall 5, the centring ribs 2.2 lie at least partially on an edge region surrounding the opening O, so that the disinfection module 1 slipping during its fastening to the wall 5 can be ruled out as far as possible.

In FIG. 7, the rear side of the wall 5 is shown with the disinfection module 1 completely fastened to the wall 5, wherein this is fastened to the wall 5 at least by means of two screws 6.

By forming the wall 5 of the storage compartment A with the removable wall section 5.1, no additional variance arises in order to arrange a disinfection module 1 in the storage compartment A as an optional extra, whereby costs and effort for integrating the disinfection module 1 can be saved.

The invention claimed is:

1. A storage assembly for a vehicle, comprising:

a storage compartment (A) for storing an object; and a wall (5);

wherein the storage compartment (A) is separated by the wall (5) from a space (R) that has a connecting element for electrical connection of a disinfection module (1) with a vehicle wiring set;

wherein the wall (5) has, for access to the connecting element, a predetermined breaking point (B) surrounding a wall section (5.1) for removing the wall section (5.1).

2. The storage assembly according to claim 1, wherein the wall (5) has a through-hole (5.3) and wherein a fastening element is insertable through the through-hole (5.3) for fastening a disinfection module (1) disposed in the storage compartment (A) to the wall (5).

3. The storage assembly according to claim 1, wherein a shaped element is formed on the wall (5) and wherein a disinfection module (1) disposed in the storage compartment (A) is fastenable on the shaped element.

4. The storage assembly according to claim 1, wherein the predetermined breaking point (B) is formed by a plurality of connection points (5.2).

5. The storage assembly according to claim 1, wherein the wall section (5.1) has a rectangular shape.

6. The storage assembly according to claim 1 in combination with a disinfection module (1), wherein the disinfection module (1) is disposed in the storage compartment (A) and wherein the disinfection module (1) has a UV-C radiation(S)-emitting light source (3) and a further connecting element (4) corresponding to the connecting element.

7. The storage assembly according to claim 6, wherein a housing (2) of the disinfection module (1) has a plurality of ventilation openings (2.1) on an underside and/or on a rear side facing the wall (5).

8. The storage assembly according to claim 6, wherein a plurality of ribs (2.2) are formed on a rear side of a housing (2) of the disinfection module (1).

9. A vehicle, comprising:

the storage assembly according to claim 1.

* * * * *